(12) United States Patent
Aksay et al.

(10) Patent No.: US 9,484,158 B2
(45) Date of Patent: Nov. 1, 2016

(54) GRAPHENE-IONIC LIQUID COMPOSITES

(71) Applicants: THE TRUSTEES OF PRINCETON UNIVERSITY, Princeton, NJ (US); VORBECK MATERIALS CORPORATION, Jessup, MD (US)

(72) Inventors: Ilhan A. Aksay, Princeton, NJ (US); Sibel Korkut, Princeton, NJ (US); Michael Pope, Princeton, NJ (US); Christian Punckt, Princeton, NJ (US)

(73) Assignees: THE TRUSTEES OF PRINCETON UNIVERSITY, Princeton, NJ (US); VORBECK MATERIALS CORPORATION, Jessup, MD (US)

( * ) Notice: Subject to any disclaimer, the term of this patent is extended or adjusted under 35 U.S.C. 154(b) by 29 days.

(21) Appl. No.: 14/379,145

(22) PCT Filed: Feb. 15, 2013

(86) PCT No.: PCT/US2013/026365
§ 371 (c)(1),
(2) Date: Aug. 15, 2014

(87) PCT Pub. No.: WO2013/123339
PCT Pub. Date: Aug. 22, 2013

(65) Prior Publication Data
US 2015/0287543 A1    Oct. 8, 2015

Related U.S. Application Data

(60) Provisional application No. 61/600,131, filed on Feb. 17, 2012.

(51) Int. Cl.
*B05D 5/12* (2006.01)
*H01G 11/04* (2013.01)
(Continued)

(52) U.S. Cl.
CPC .............. *H01G 11/04* (2013.01); *B82Y 30/00* (2013.01); *B82Y 40/00* (2013.01); *C01B 31/0446* (2013.01); *C01B 31/0484* (2013.01);
(Continued)

(58) Field of Classification Search
USPC .......................... 427/79–81; 29/25.41, 25.42
See application file for complete search history.

(56) References Cited

U.S. PATENT DOCUMENTS 7,180,725 B2    2/2007   Takeuchi et al.
7,658,901 B2    2/2010   Prud'Homme et al.
(Continued)

FOREIGN PATENT DOCUMENTS

WO    WO 2011/029006    *  3/2011
WO    WO 2011/078585    *  6/2011

OTHER PUBLICATIONS

U.S. Appl. No. 14/515,019, filed Oct. 15, 2014, Prud'Homme, et al.
(Continued)

*Primary Examiner* — Brian K Talbot
(74) *Attorney, Agent, or Firm* — Oblon, McClelland, Maier & Neustadt, L.L.P.

(57) ABSTRACT

Method of making a graphene-ionic liquid composite. The composite can be used to make elec-trodes for energy storage devices, such as batteries and supercapacitors. Disclosed and claimed herein is method of making a graphene-ionic liquid com-posite, comprising combining a graphene source with at least one ionic liquid and heating the combination at a temperature of at least about 130 °C.

15 Claims, 2 Drawing Sheets

(51) Int. Cl.

| | | |
|---|---|---|
| *B82Y 30/00* | (2011.01) | |
| *C01B 31/04* | (2006.01) | |
| *B82Y 40/00* | (2011.01) | |
| *H01M 4/133* | (2010.01) | |
| *H01G 11/28* | (2013.01) | |
| *H01G 11/36* | (2013.01) | |
| *H01G 11/38* | (2013.01) | |
| *H01G 11/24* | (2013.01) | |
| *H01G 11/34* | (2013.01) | |
| *H01G 11/44* | (2013.01) | |
| *H01G 11/86* | (2013.01) | |
| *C08L 25/06* | (2006.01) | |
| *C08K 3/04* | (2006.01) | |

(52) U.S. Cl.
CPC ............ *H01G 11/24* (2013.01); *H01G 11/28* (2013.01); *H01G 11/34* (2013.01); *H01G 11/36* (2013.01); *H01G 11/38* (2013.01); *H01G 11/44* (2013.01); *H01G 11/86* (2013.01); *H01M 4/133* (2013.01); *C01B 2204/32* (2013.01); *C08K 3/04* (2013.01); *C08L 25/06* (2013.01); *Y02E 60/122* (2013.01); *Y02E 60/13* (2013.01); *Y02P 70/54* (2015.11)

(56) References Cited

U.S. PATENT DOCUMENTS

| | | | |
|---|---|---|---|
| 7,659,350 | B2 | 2/2010 | Prud'Homme et al. |
| 7,745,528 | B2 | 6/2010 | Prud'Homme et al. |
| 7,771,824 | B2 | 8/2010 | Herrera-Alonso et al. |
| 7,935,754 | B2 | 5/2011 | Prud'Homme et al. |
| 8,047,248 | B2 | 11/2011 | Prud'Homme et al. |
| 8,048,214 | B2 | 11/2011 | Prud'Homme et al. |
| 8,048,931 | B2 | 11/2011 | Prud'Homme et al. |
| 8,048,950 | B2 | 11/2011 | Prud'Homme et al. |
| 8,053,508 | B2 | 11/2011 | Korkut et al. |
| 8,063,134 | B2 | 11/2011 | Prud'Homme et al. |
| 8,066,964 | B2 | 11/2011 | Prud'Homme et al. |
| 8,105,976 | B2 | 1/2012 | Prud'Homme et al. |
| 8,110,026 | B2 | 2/2012 | Prud'Homme et al. |
| 8,110,524 | B2 | 2/2012 | Prud'Homme et al. |
| 8,192,870 | B2 | 6/2012 | Aksay et al. |
| 8,278,757 | B2 | 10/2012 | Crain et al. |
| 8,449,959 | B2 | 5/2013 | Aksay et al. |
| 8,697,485 | B2 | 4/2014 | Crain et al. |
| 2009/0146111 | A1* | 6/2009 | Shin ............... B82Y 30/00 252/510 |
| 2009/0233057 | A1 | 9/2009 | Aksay et al. |
| 2009/0246625 | A1* | 10/2009 | Lu ............... H01M 4/133 429/207 |
| 2009/0272946 | A1* | 11/2009 | Lu ............... H01B 1/04 252/511 |
| 2010/0303706 | A1 | 12/2010 | Wallace et al. |
| 2011/0049437 | A1 | 3/2011 | Crain et al. |
| 2011/0114897 | A1 | 5/2011 | Aksay et al. |
| 2011/0178224 | A1 | 7/2011 | Pan et al. |
| 2011/0287316 | A1* | 11/2011 | Lu ............... B82Y 30/00 429/215 |
| 2012/0026643 | A1* | 2/2012 | Yu ............... H01G 11/02 361/502 |
| 2012/0088084 | A1 | 4/2012 | Prud'Homme et al. |
| 2012/0111599 | A1* | 5/2012 | Roberson ............... H01B 1/04 174/107 |
| 2012/0145234 | A1 | 6/2012 | Roy-Mayhew et al. |
| 2012/0237749 | A1 | 9/2012 | Aksay et al. |
| 2012/0244333 | A1 | 9/2012 | Aksay et al. |
| 2012/0255607 | A1 | 10/2012 | Roy-Mayhew et al. |
| 2012/0256138 | A1* | 10/2012 | Suh ............... B82Y 30/00 252/503 |
| 2013/0180912 | A1* | 7/2013 | Li ............... B01D 67/0079 210/500.21 |
| 2013/0302588 | A1 | 11/2013 | Aksay et al. |
| 2014/0079932 | A1 | 3/2014 | Aksay et al. |
| 2014/0177178 | A1 | 6/2014 | Crain et al. |
| 2014/0302373 | A1* | 10/2014 | Lockett ............... C07D 233/58 429/124 |

OTHER PUBLICATIONS

U.S. Appl. No. 14/555,955, filed Nov. 28, 2014, Roy-Mayhew, et al.
U.S. Appl. No. 14/736,838, filed Jun. 11, 2015, Aksay, et al.
U.S. Appl. No. 14/689,638, filed Apr. 17, 2015, Crain, et al.
U.S. Appl. No. 14/739,184, filed Jun. 15, 2015, Pope, et al.
U.S. Appl. No. 14/751,418, filed Jun. 26, 2015, Crain, et al.
International Search Report issued Apr. 19, 2013, in PCT/US13/026365 filed Feb. 15, 2013.
Tung, et al., Poly(ionic liquid)-stabilized graphene sheets and their hybrid with poly(3,4-ethylenedioxythiophene), Organic Electronics 12, Elsevier, 2011, 10 pages.
Kim, et al., "High-Performance Supercapacitors Based on Poly(ionic liquid)—Modified Graphene Electrodes", ACS Nano, vol. 5, No. 1, Dec. 13, 2010, pp. 436-442.

* cited by examiner

GRAPHENE-IONIC LIQUID COMPOSITES

The present application claims priority under 35 U.S.C. 119(e) to U.S. Ser. No. 61/600,131, filed Feb. 17, 2012, the entire contents of which are incorporated herein by reference.

STATEMENT REGARDING FEDERALLY SPONSORED RESEARCH AND DEVELOPMENT

This invention was made with government support under Grant No. FA9550-09-1-0523 awarded by the U.S. Air Force Office of Scientific Research; Subaward No. 66354 from Battelle-Pacific Northwest National Lab, Battelle's Prime Grant from the Department of Energy, Award No. DE-AC05-76RL01830; Grant No. W911 NF-09-1-0476 awarded by the U.S. Army (RD&E Command); and Contract No. W911QX-11-C-0079 awarded by the U.S. Army. The government has certain rights in this invention.

FIELD OF THE INVENTION

The present invention relates to graphene-ionic liquid composites, their methods of manufacture, electrodes made therefrom, and energy storage devices containing the composites.

BACKGROUND

The growing use of cordless devices such portable electronic devices and power tools as well as the increasing need for high capacity energy storage for uses such as electrical vehicles has driven significant research into low-cost, high efficiency, high energy density energy storage devices such as batteries and capacitors (including supercapacitors). Graphene is a promising material for use in such devices, but many graphene-containing devices lack the necessary properties for practical use.

US patent application publication 2011/0080689 discloses ionic liquids for use in ultracapacitors and graphene-based ultracapacitors. *ACS Nano* 2010, 4, 1227 discloses the exfoliation of graphite oxide in propylene carbonate and thermal reduction of the resulting graphene oxide. *ACS Nano* 2011, 5, 436 discloses high-performance supercapacitors based on poly(ionic liquid)-modified graphene electrodes. *Adv. Mater.* 2011, 23, 2833 discloses graphene films used in high-performance supercapacitors. *Nano Lett.* 2010, 10, 4863 discloses graphene-based supercapacitors with an ultrahigh energy density.

SUMMARY OF THE INVENTION

Disclosed and claimed herein is method of making a graphene-ionic liquid composite, comprising combining a graphene source with at least one ionic liquid and heating the combination at a temperature of at least about 130° C. Further disclosed and claimed is a method of making an electrode, comprising combining a graphene source with at least one ionic liquid, coating the combination onto a substrate and heating the combination at a temperature of at least about 130° C. and electrodes made by the method.

DETAILED DESCRIPTION OF THE INVENTION

Figure 1:
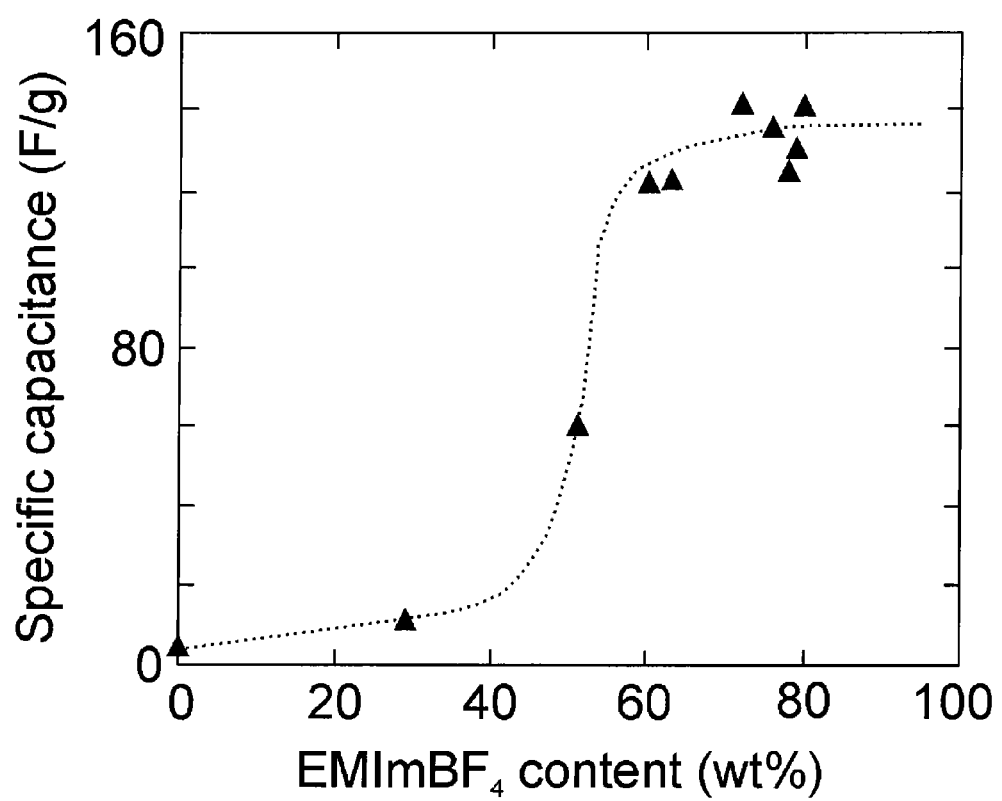
FIG. 1 is a plot showing the specific capacitance of coassembled and thermally reduced composites of graphene oxide with varying amounts of the ionic liquid 1-ethyl-2-methylimidazolium tetrafluoroborate.

At least one graphene source is combined with at least one ionic liquid and the resulting dispersion is heated to produce a composite containing graphene and at least one ionic liquid. Examples of graphene sources include graphite oxide and graphene.

The graphene source-ionic liquid dispersion can contain one or more solvents. The ionic liquid can be dissolved or suspended in a solvent. The resulting blend can be applied to a substrate and then heated to remove volatile components (such as solvents). The blend can be in the form of a gel, slurry, etc. Heating reduces graphite oxide to graphene and can reduce or anneal graphene.

Solvents are compounds other than ionic liquids. Examples of solvents include water, ammoniated water, organic solvents, alcohols (such as ethanol), water/alcohol mixtures (such as ethanol/water), esters and carbonates (such as ethylene carbonate, propylene carbonate), dimethylformamide (DMF), N-methylpyrrolidone (NMP), acetonitrile, dimethylsulfoxide (DMSO), etc. Surfactants can be added to the dispersions. In some embodiments, the solvent is present in the dispersion in about 70 to about 99.9 weight percent, or about 80 to about 99.9 weight percent, or about 90 to about 99.9 weight percent, or about 90 to about 99.5 weight percent, or about 95 to about 99.9 weight percent, or about 95 to about 99.5 weight percent, based on the total weight of solvent and ionic liquid The graphene source dispersions and their blends with ionic liquids can be formed using any suitable mixing method, including ultrasonication, stirring, milling, grinding, attrition, etc. High-shear mixers, ball mills, attrition equipment, sandmills, two-roll mills, three-roll mills, cryogenic grinding crushers, double planetary mixers, triple planetary mixers, high pressure homogenizers, horizontal and vertical wet grinding mills, etc. can be used to form the dispersions and blends. Examples of media that can be used for mixing include metals, carbon steel, stainless steel, ceramics, stabilized ceramic media (such as cerium yttrium stabilized zirconium oxide), PTFE, glass, tungsten carbide, etc. The graphene source can be dispersed in solvent prior to combining it with ionic liquid, or it can be blended (undispersed, such as dry blended) with the ionic liquid, and optionally, solvent, and the resulting combination can be well-mixed using a method such as one of those disclosed above. Graphene source dispersions can be formed by generating graphite oxide or graphene from precursor materials (such as graphite or graphite oxide) in a solvent. These dispersions can be used as they are made, concentrated, purified, be treated with other additives, etc.

In some embodiments of the invention, the ionic liquid is present in about 10 to about 99.9 weight percent, or about 20 to about 99.9 weight percent, or about 25 to about 99.9 weight percent, or about 30 to about 99.9 weight percent, or about 40 to about 99.9 weight percent, or about 50 to about 99.9 weight percent, or about 60 to about 99.9 weight percent, or about 70 to about 99.9 weight percent, or about 20 to about 95 weight percent, or about 30 to about 95 weight percent, or about 40 to about 95 weight percent, or about 50 to about 95 weight percent, or about 60 to about 95 weight percent, based on the total weight of ionic liquid and graphene source.

The graphene source-ionic liquid dispersions can be coated onto (applied to) a substrate using any suitable method. Examples of application methods include, but are not limited to, painting, pouring, tape casting, spin casting, solution casting, dip coating, powder coating, by syringe or pipette, spray coating, curtain coating, lamination, co-extrusion, electrospray deposition, ink-jet printing, spin coating, thermal transfer (including laser transfer) methods, doctor blade printing, screen printing, rotary screen printing, gravure printing, lithographic printing, intaglio printing, digital printing, capillary printing, offset printing, electrohydrodynamic (EHD) printing, microprinting, pad printing, tampon printing, stencil printing, wire rod coating, drawing, flexographic printing, stamping, xerography, microcontact printing, dip pen nanolithography, laser printing, via pen or similar means, etc. The dispersions can be applied in multiple layers.

Examples of substrates include electrically conductive substrates such as metals (such as aluminum, copper, steel, stainless steel, etc.), carbon-based materials (such expanded or expandable graphite (such as Grafoil®), graphite, etc.), carbon coated materials, metal coated materials, indium tin oxide or antimony tin oxide coated materials, etc. The substrate can be a current collector, such as that used in a battery, capacitor, supercapacitor, or the like.

Substrates can comprise flexible and/or stretchable materials, silicones and other elastomers and other polymeric materials, fabrics (including cloths) and textiles (such as cotton, wool, polyesters, rayon, etc.), glasses and other minerals, ceramics, silicon surfaces, wood, paper, cardboard, paperboard, cellulose-based materials, silicon and other semiconductors, laminates, corrugated materials, etc. Substrates can in the form of films, papers, wafers, larger three-dimensional objects, etc. They can be in woven, non-woven, in a mesh form. The substrates can be coated materials, such as any of the above types of substrate that have been coated. Preferred coatings include electrically-conductive coatings.

Examples of polymeric materials include, but are not limited to, those comprising thermoplastics and thermosets, including elastomers and rubbers (including thermoplastics and thermosets), silicones, fluorinated polysiloxanes, polyesters (such as poly(ethylene terephthalate), poly(butylene terephthalate), poly(ethylene naphthalate), liquid crystalline polyesters, polyamides (including polyterephthalamides); polyimides (such as Kapton®), aramids (such as Kevlar® and Nomex®); fluoropolymers (such as fluorinated ethylene propylene (FEP), polytetrafluoroethylene (PTFE), poly(vinyl fluoride), poly(vinylidene fluoride), etc.), hexafluoropropylene/vinylidene fluoride/tetrafluoroethylene copolymers, tetrafluoroethylene/propylene copolymers, fluorelastomers, polyetherimides, thermoset epoxies and polyurethanes; polyolefins (such as polyethylene (including high density polyethylene, ultrahigh molecular weight polyethylene (UHMWPE), etc.).

The dispersions are heated to remove solvent and form the composites of the invention. When the graphene source includes graphite oxide, the graphite oxide is reduced to graphene. When the graphene source includes graphene, the graphene can be further reduced, annealed, etc. upon heating. Solvent removal (drying) can be done prior to reduction of graphite oxide or further heat treatment of graphene, or both can be done in the same step. Heat treating is preferably done in an inert atmosphere. The temperatures can be from about 130° C. to about 450° C., or about 140° C. to about 450° C., or about 150° C. to about 450° C., or about 150° C. to about 400° C., or about 175° C. to about 400° C., or about 200° C. to about 450° C.

After heating, the composites preferably contain no more than about 30 weight percent solvent, or no more than about 20 weight percent solvent, or no more than about 10 weight percent solvent, or no more than about 5 weight percent solvent, or no more than about 3 weight percent solvent, or no more than about 1 weight percent solvent, or no more than about 0.1 weight percent solvent, or no more than about 0.01 weight percent solvent, or no more than about 0.001 weight percent solvent.

The heating can be for any suitable duration, such as for seconds to many hours. For example, in cases where the ionic liquid is susceptible to degradation or high throughput is needed, heating may be done for seconds or a few minutes. In some cases it may be necessary to heat for several minutes or hours, such as, for example, when it is necessary to remove sufficient amounts of solvent or to reduce the graphite oxide or graphene to a desired degree. In some cases, the atmosphere during heating is saturated with ionic liquid vapor.

The dispersions can contain additional electrically conductive additives. Examples of additives include such as metals (including metal alloys), conductive metal oxides, polymers, carbonaceous materials other than the graphene source, metal-coated materials, etc. These components can take a variety of forms, including particles, powders, flakes, foils, needles, etc.

Examples of metals include, but are not limited to silver, copper, aluminum, platinum, palladium, nickel, chromium, gold, bronze, colloidal metals, etc. Examples of metal oxides include antimony tin oxide and indium tin oxide and materials such as fillers coated with metal oxides. Metal and metal-oxide coated materials include, but are not limited to metal coated carbon and graphite fibers, metal coated glass fibers, metal coated glass beads, metal coated ceramic materials (such as beads), etc. These materials can be coated with a variety of metals, including nickel.

Examples of electrically conductive polymers include, but are not limited to, polyacetylene, polyethylene dioxythiophene (PEDOT), poly(styrenesulfonate) (PSS), PEDOT: PSS copolymers, polythiophene and polythiophenes, poly (3-alkylthiophenes), poly(2,5-bis(3-tetradecylthiophen-2-yl)thieno[3,2-b]thiophene) (PBTTT), poly (phenylenevinylene), polypyrene, polycarbazole, polyazulene, polyazepine, polyflurorenes, polynaphthalene, polyisonaphthalene, polyaniline, polypyrrole, poly(phenylene sulfide), copolymers of one or more of the foregoing, etc., and their derivatives and copolymers. The conductive polymers can be doped or undoped. They can be doped with boron, phosphorous, iodine, etc.

Examples of carbonaceous materials other than the graphene source include, but are not limited to, graphitized carbon, carbon black, carbon fibers and fibrils, carbon whiskers, vapor-grown carbon nanofibers, metal coated carbon fibers, carbon nanotubes (including single- and multi-walled nanotubes), fullerenes, activated carbon, carbon fibers, expanded graphite, expandable graphite, hollow carbon spheres, carbon foams, etc.

The ionic liquids are preferably salts having a melting point below about 100° C. They are preferably monomeric.

Examples of ionic liquids are those based on ammonium, imidazolium (including alkyl (such as methyl) substituted), phosphonium, pyrazolium (including alkyl (such as methyl) substituted), pyridinium (including alkyl (such as methyl)

substituted), pyrolidinium (including alkyl (such as methyl) substituted), sulfonium, triazolium (such as 1,3-dialkyl-1,2,3-triazolium), choline, piperidinium, imide, morpholium, etc. cations.

Ionic liquids can be based on halide (such as chloride, bromide, etc.), trihalogenoaluminate, phosphate (such as hexafluorophosphate), borate (such as tetrafluoroborate), triflate, tosylate, bistriflimide, dicyanamide, formate, acetate, trifluoro acetate, methyl carbonate, alkylsulfate, alkylphosphate, glycolate, nitrate, hydroxide, etc. anions.

Examples include 1-ethyl-2-methylimidazolium tetrafluoroborate (EMImBF$_4$), 1-alkyl-3-methylimidazoliumtetrafluoroborate (such as 1-butyl-3-methylimidazoliumtetrafluoroborate), 1-butyl-3-methylimidazolium hexafluorophosphate ([BMIM][PF$_6$]), 1-butyl-3-methylimidazolium hydroxide ([bmim]OH), 1-ethyl-3-methylimidazolium dicyanamide, 1-butyl-3-methylimidazolium chloride, 1-butyl-3-methylimidazolium hexafluorophosphate, trioctylmethylammonium bis(trifluoromethyl-sulfonyl) imide, 1-butyl-3-methylimidazolium chloride, 2-Hydroxyethylammonium formate, 1,3-dialkyl-1,2,3-triazolium hexafluorophosphates, 1,3-dialkyl-1,2,3-triazolium bistriflimides, 1,3-dialkylimidazolium hexafluorophosphates, 1,3-dialkyl-1,2,3-triazolium bistriflimides, triethylsulfonium bis(trifluoromethylsulfonyl)imide, bis(pentafluoroethylsulfonyl)imide, 1-butyl-1-methylpiperidinium tetrafluoroborate, choline acetate, 1-butyl-1-methylpiperidinium hexafluorophosphate, 4-ethyl-4-methylmorpholinium methyl carbonate 1-ethyl-1-methylpiperidinium methyl carbonate, triethylsulfonium bis(trifluoromethylsulfonyl)imide, 2-hydroxyethylammonium formate, Graphite oxide (also known as graphitic acid or graphene oxide) can be produced by any method known in the art, such as by a process that involves oxidation of graphite using one or more chemical oxidizing agents and, optionally, intercalating agents such as sulfuric acid. Examples of oxidizing agents include nitric acid, sodium and potassium nitrates, perchlorates, hydrogen peroxide, sodium and potassium permanganates, phosphorus pentoxide, bisulfites, etc. Preferred oxidants include KClO$_4$; HNO$_3$ and KClO$_3$; KMnO$_4$ and/or NaMnO$_4$; KMnO$_4$ and NaNO$_3$; K$_2$S$_2$O$_8$ and P$_2$O$_5$ and KMnO$_4$; KMnO$_4$ and HNO$_3$; and HNO$_3$. Preferred intercalation agents include sulfuric acid. Graphite can also be treated with intercalating agents and electrochemically oxidized. Examples of methods of making graphite oxide include those described by Staudenmaier (*Ber. Stsch. Chem. Ges.* (1898), 31, 1481) and Hummers (*J. Am. Chem. Soc.* (1958), 80, 1339). Graphite oxide can be used in the form of isolated dry material, a slurry/dispersion/suspension in a solvent, etc.

As used herein, the term "graphene" refers to graphite sheets preferably having a surface area of from about 100 to about 2630 m$^2$/g. In some embodiments, the graphene primarily, almost completely, or completely comprises single-carbon atom thick fully exfoliated single planar sheets of graphite (these are approximately ≤1 nm thick), while in other embodiments, at least a portion of the graphene can comprise partially exfoliated graphite sheets, in which two or more sheets of graphite have not been exfoliated from each other. The graphene can comprise mixtures of fully and partially exfoliated graphite sheets. Graphene is distinct from carbon nanotubes. Graphene can have a "platey" (e.g. two-dimensional) structure and does not have the needle-like form of carbon nanotubes. The two longest dimensions of the graphene can each be at least about 10 times greater, or at least about 50 times greater, or at least about 100 times greater, or at least about 1000 times greater, or at least about 5000 times greater, or at least about 10,000 times greater than the shortest dimension (i.e. thickness) of the sheets.

Graphene can be made using any suitable method. For example, it can be obtained from graphite, graphite oxide, expandable graphite, expanded graphite, etc. It can be obtained by the physical exfoliation of graphite, by for example, peeling, grinding, or milling off graphene. It can be made from inorganic precursors, such as silicon carbide. It can be made by chemical vapor deposition (such as by reacting a methane and hydrogen on a metal surface). It can be made by the reduction of an alcohol, such ethanol, with a metal (such as an alkali metal like sodium) and the subsequent pyrolysis of the alkoxide product (such a method is reported in *Nature Nanotechnology* (2009), 4, 30-33). It can be made by the exfoliation of graphite in dispersions or exfoliation of graphite oxide in dispersions and the subsequently reducing the exfoliated graphite oxide. Graphene can be made by the exfoliation of expandable graphite, followed by intercalation, and ultrasonication or other means of separating the intercalated sheets (see, for example, *Nature Nanotechnology* (2008), 3,538-542). It can be made by the intercalation of graphite and the subsequent exfoliation of the product in suspension, thermally, etc.

Graphite can be treated with oxidizing and/or intercalating agents and exfoliated to form graphene. Graphite can also be treated with intercalating agents and electrochemically oxidized and exfoliated. Graphene can be formed by ultrasonically exfoliating suspensions of graphite and/or graphite oxide in a liquid (which can contain surfactants and/or intercalants). Exfoliated graphite oxide dispersions or suspensions can be subsequently reduced to graphene. Graphene can also be formed by mechanical treatment (such as grinding or milling) to exfoliate graphite or graphite oxide (which would subsequently be reduced to graphene).

Reduction of graphite oxide to graphene can be by means of chemical reduction and can be carried out on graphite oxide in a solid form, in a dispersion, etc. Examples of useful chemical reducing agents include, but are not limited to, hydrazines (such as hydrazine, N,N-dimethylhydrazine, etc.), sodium borohydride, citric acid, hydroquinone, isocyanates (such as phenyl isocyanate), hydrogen, hydrogen plasma, etc. A dispersion or suspension of exfoliated graphite oxide in a carrier (such as water, organic solvents, or a mixture of solvents) can be made using any suitable method (such as ultrasonication and/or mechanical grinding or milling) and reduced to graphene.

One example of a method for the preparation of graphene is to oxidize graphite to graphite oxide, which is then thermally exfoliated to form graphene (also known as thermally exfoliated graphite oxide), as described in US 2007/0092432, the disclosure of which is hereby incorporated herein by reference. The thusly formed graphene can display little or no signature corresponding to graphite or graphite oxide in their X-ray diffraction pattern.

The thermal exfoliation can be carried out in a continuous, semi-continuous batch, etc. process. Heating can be done in a batch process or a continuous process and can be done under a variety of atmospheres, including inert and reducing atmospheres (such as nitrogen, argon, and/or hydrogen atmospheres). Heating times can range from under a few seconds or several hours or more, depending on the temperatures used and the characteristics desired in the final thermally exfoliated graphite oxide. Heating can be done in any appropriate vessel, such as a fused silica, mineral, metal, carbon (such as graphite), ceramic, etc. vessel. Heating can be done using a flash lamp. During heating, the graphite oxide can be contained in an essentially constant location in single batch reaction vessel, or can be transported through one or more vessels during the reaction in a continuous or batch mode. Heating can be done using any suitable means, including the use of furnaces and infrared heaters.

Examples of temperatures at which the thermal exfoliation of graphite oxide can be carried out are at least about 300° C., at least about 400° C., at least about 450° C., at least about 500° C., at least about 600° C., at least about 700° C., at least about 750° C., at least about 800° C., at least about 850° C., at least about 900° C., at least about 950° C., and at least about 1000° C. Preferred ranges include between about 750 about and 3000° C., between about 850 and 2500° C., between about 950 and about 2500° C., and between about 950 and about 1500° C.

The time of heating can range from less than a second to many minutes. For example, the time of heating can be less than about 0.5 seconds, less than about 1 second, less than about 5 seconds, less than about 10 seconds, less than about 20 seconds, less than about 30 seconds, or less than about 1 min. The time of heating can be at least about 1 minute, at least about 2 minutes, at least about 5 minutes, at least about 15 minutes, at least about 30 minutes, at least about 45 minutes, at least about 60 minutes, at least about 90 minutes, at least about 120 minutes, at least about 150 minutes, at least about 240 minutes, from about 0.01 seconds to about 240 minutes, from about 0.5 seconds to about 240 minutes, from about 1 second to about 240 minutes, from about 1 minute to about 240 minutes, from about 0.01 seconds to about 60 minutes, from about 0.5 seconds to about 60 minutes, from about 1 second to about 60 minutes, from about 1 minute to about 60 minutes, from about 0.01 seconds to about 10 minutes, from about 0.5 seconds to about 10 minutes, from about 1 second to about 10 minutes, from about 1 minute to about 10 minutes, from about 0.01 seconds to about 1 minute, from about 0.5 seconds to about 1 minute, from about 1 second to about 1 minute, no more than about 600 minutes, no more than about 450 minutes, no more than about 300 minutes, no more than about 180 minutes, no more than about 120 minutes, no more than about 90 minutes, no more than about 60 minutes, no more than about 30 minutes, no more than about 15 minutes, no more than about 10 minutes, no more than about 5 minutes, no more than about 1 minute, no more than about 30 seconds, no more than about 10 seconds, or no more than about 1 second. During the course of heating, the temperature can vary.

Examples of the rate of heating include at least about 120° C./min, at least about 200° C./min, at least about 300° C./min, at least about 400° C./min, at least about 600° C./min, at least about 800° C./min, at least about 1000° C./min, at least about 1200° C./min, at least about 1500° C./min, at least about 1800° C./min, and at least about 2000° C./min.

Graphene can be annealed or reduced to graphene having higher carbon to oxygen ratios by heating under reducing atmospheric conditions (e.g., in systems purged with inert gases or hydrogen). Reduction/annealing temperatures are preferably at least about 300° C., or at least about 350° C., or at least about 400° C., or at least about 500° C., or at least about 600° C., or at least about 750° C., or at least about 850° C., or at least about 950° C., or at least about 1000° C. The temperature used can be, for example, between about 750 about and 3000° C., or between about 850 and 2500° C., or between about 950 and about 2500° C.

The time of heating can be for example, at least about 1 second, or at least about 10 second, or at least about 1 minute, or at least about 2 minutes, or at least about 5 minutes. In some embodiments, the heating time will be at least about 15 minutes, or about 30 minutes, or about 45 minutes, or about 60 minutes, or about 90 minutes, or about 120 minutes, or about 150 minutes. During the course of annealing/reduction, the temperature can vary within these ranges.

The heating can be done under a variety of conditions, including in an inert atmosphere (such as argon or nitrogen) or a reducing atmosphere, such as hydrogen (including hydrogen diluted in an inert gas such as argon or nitrogen), or under vacuum. The heating can be done in any appropriate vessel, such as a fused silica or a mineral or ceramic vessel or a metal vessel. The materials being heated including any starting materials and any products or intermediates) can be contained in an essentially constant location in single batch reaction vessel, or can be transported through one or more vessels during the reaction in a continuous or batch reaction. Heating can be done using any suitable means, including the use of furnaces and infrared heaters.

The graphene preferably has a surface area of at least about 100 m$^2$/g to, or of at least about 200 m$^2$/g, or of at least about 300 m$^2$/g, or of least about 350 m$^2$/g, or of least about 400 m$^2$/g, or of least about 500 m$^2$/g, or of least about 600 m$^2$/g., or of least about 700 m$^2$/g, or of least about 800 m$^2$/g, or of least about 900 m$^2$/g, or of least about 700 m$^2$/g. The surface area can be about 400 to about 1100 m$^2$/g. The theoretical maximum surface area can be calculated to be 2630 m$^2$/g. The surface area includes all values and subvalues there between, especially including 400, 500, 600, 700, 800, 900, 1000, 1100, 1200, 1300, 1400, 1500, 1600, 1700, 1800, 1900, 2000, 2100, 2200, 2300, 2400, 2500, and 2630 m$^2$/g.

The graphene can have number average aspect ratios of about 100 to about 100,000, or of about 100 to about 50,000, or of about 100 to about 25,000, or of about 100 to about 10,000 (where "aspect ratio" is defined as the ratio of the longest dimension of the sheet to the shortest).

Surface area can be measured using either the nitrogen adsorption/BET method at 77 K or a methylene blue (MB) dye method in liquid solution.

The dye method is carried out as follows: A known amount of graphene is added to a flask. At least 1.5 g of MB are then added to the flask per gram of graphene. Ethanol is added to the flask and the mixture is ultrasonicated for about fifteen minutes. The ethanol is then evaporated and a known quantity of water is added to the flask to re-dissolve the free MB. The undissolved material is allowed to settle, preferably by centrifuging the sample. The concentration of MB in solution is determined using a UV-vis spectrophotometer by measuring the absorption at $\lambda_{max}$=298 nm relative to that of standard concentrations.

The difference between the amount of MB that was initially added and the amount present in solution as determined by UV-vis spectrophotometry is assumed to be the amount of MB that has been adsorbed onto the surface of the graphene. The surface area of the graphene is then calculated using a value of 2.54 m$^2$ of surface covered per one mg of MB adsorbed.

The graphene can have a bulk density of from about 0.01 to at least about 200 kg/m$^3$. The bulk density includes all values and subvalues therebetween, especially including 0.05, 0.1, 0.5, 1, 5, 10, 15, 20, 25, 30, 35, 50, 75, 100, 125, 150, and 175 kg/m$^3$.

The graphene can be functionalized with, for example, oxygen-containing functional groups (including, for example, hydroxyl, carboxyl, and epoxy groups) and typically have an overall carbon to oxygen molar ratio (C/O ratio), as determined by bulk elemental analysis, of at least about 1:1, or more preferably, at least about 3:2. Examples of carbon to oxygen ratios include about 3:2 to about 85:15; about 3:2 to about 20:1; about 3:2 to about 30:1; about 3:2 to about 40:1; about 3:2 to about 60:1; about 3:2 to about 80:1; about 3:2 to about 100:1; about 3:2 to about 200:1; about 3:2 to about 400:1; about 3:2 to about 500:1; about 3:2 to about 1000:1; about 3:2 to greater than 1000:1; about 3:1 to about 30:1; about 3:1 to about 20:1; about 3:1 to about 15:1; about 10:1 to about 30:1; about 80:1 to about 100:1; about 20:1 to about 100:1; about 20:1 to about 500:1; about 20:1 to about 1000:1; about 50:1 to about 300:1; about 50:1 to about 500:1; and about 50:1 to about 1000:1. In some embodiments, the carbon to oxygen ratio is at least about 10:1, or at least about 15:1, or at least about 20:1, or at least about 35:1, or at least about 50:1, or at least about 75:1, or at least about 100:1, or at least about 200:1, or at least about 300:1, or at least about 400:1, or at least 500:1, or at least about 750:1, or at least about 1000:1; or at least about 1500:1, or at least about 2000:1. The carbon to oxygen ratio also includes all values and subvalues between these ranges.

The graphene can contain atomic scale kinks. These kinks can be caused by the presence of lattice defects in, or by chemical functionalization of the two-dimensional hexagonal lattice structure of the graphite basal plane.

The composite can be electrically conductive. It can have a conductivity of at least about $10^{-8}$ S/m. It can have a conductivity of about $10^{-6}$ S/m to about $10^5$ S/m, or of about $10^{-5}$ S/m to about $10^5$ S/m. In other embodiments of the invention, the coating has conductivities of at least about 0.001 S/m, of at least about 0.01 S/m, of at least about 0.1 S/m, of at least about 1 S/m, of at least about 10 S/m, of at least about 100 S/m, or at least about 1000 S/m, or at least about 10,000 S/m, or at least about 20,000 S/m, or at least about 30,000 S/m, or at least about 40,000 S/m, or at least about 50,000 S/m, or at least about 60,000 S/m, or at least about 75,000 S/m, or at least $10^5$ S/m, or at least about $10^6$ S/m.

In some embodiments, the surface resistivity of the composite may be no greater than about 10000 Ω/square/mil, or no greater than about 5000 Ω/square/mil, or no greater than about 1000 Ω/square/mil or no greater than about 700 Ω/square/mil, or no greater than about 500 Ω/square/mil, or no greater than about 350 Ω/square/mil, or no greater than about 200 Ω/square/mil, or no greater than about 200 Ω/square/mil, or no greater than about 150 Ω/square/mil, or no greater than about 100 Ω/square/mil, or no greater than about 75 Ω/square/mil, or no greater than about 50 Ω/square/mil, or no greater than about 30 Ω/square/mil, or no greater than about 20 Ω/square/mil, or no greater than about 10 Ω/square/mil, or no greater than about 5 Ω/square/mil, or no greater than about 1 Ω/square/mil, or no greater than about 0.1 Ω/square/mil, or no greater than about 0.01 Ω/square/mil, or no greater than about 0.001 Ω/square/mil.

The composites and substrates coated with the composites can be used in energy storage applications, electrochemical sensors, electromechanical actuators, etc. Examples of energy storage devices include batteries (such as electrodes for use in rechargeable, lithium ion, lithium polymer, lithium air, etc. batteries), capacitors (including supercapacitors (also called ultracapacitors or electrochemical double-layer capacitors)), fuel cells, etc. They can be used as electrodes, current collectors, etc.

In some cases, the ionic liquid serves both as a spacer between the graphene sheets and an electrolyte.

In some embodiments, the single electrode capacitance of the capacitors is about 0.1 to about 550, or about 10 to about 550, or about 50 to about 550, or about 75 to about 550, or about 100 to about 550, or about 120 to about 550 F/g.

Energy storage devices can be used in any suitable equipment, apparatus, device, etc. Examples include portable electronic devices such as computers, cellular telephones, games, navigation systems, personal digital assistants, music players, mp3 players, games, calculators, radios, touch pad devices, artificial "paper" and reading devices, etc. The batteries can be used in vehicles, such as all-electric and hybrid vehicles, cars, trucks, minivans, SUVs, buses, snowmobiles, all-terrain vehicles, motorcycles, mopeds, electric bicycles, scooters, submersibles, tanks, forklifts, construction equipment, aircraft, submarines, train engines, trams, space exploration equipment, satellites, etc. They can be used in flashlights, medical equipment, robots, power tools, landscaping equipment (such as lawnmowers, trimmers, edgers, etc.), chain saws, etc. They can be used in lighting devices (such as flash lights, spot lights, flood lights, etc.), military equipment, night vision goggles, rangefinders, target identifiers, etc. They can be used in solar energy systems, backup power for memory, uninterrupted power supply applications, regenerative braking systems, doors and evacuation slides for aircraft, motor starters, HVAC equipment, radar pulse power, cold engine starting, etc. They can be used as one or more components of dual battery/capacitor systems.

EXAMPLES

Synthesis of Graphene Oxide

Graphene oxide (GO) was produced according to a modified Hummer's method (Marcano et al. *ACS Nano* 2010, 4, 4806). 3 g of natural flake graphite (Asbury 3061) and 18 g of $KMnO_4$ were added under stirring into 360 mL of $H_2SO_4$ and 40 mL of $H_3PO_4$. The reaction was held at 50° C. for approximately 16 hrs. The reaction was then cooled and added to approximately 400 mg. 6 mL of $H_2O_2$ was then added after which the suspension turned a bright yellow color. The suspension was split into two 500 mL centrifuge tubes and spun at 3500 RPM for 15 min using an IEC Centra GP8R centrifuge (218A rotor). The supernatant was discarded and the material was resuspended with water. This washing procedure was then repeated with 250 mL of HCl and again with ethanol three to four times until elemental analysis (by energy dispersive X-ray spectroscopy (EDS)) showed no change in residual chloride.

Electrode Fabrication

Ethanol was used to dilute the GO/ethanol pellet to a concentration of approximately 10 mg/mL. The electrode precursor suspension was prepared by mixing this ethanol slurry with deionized water at a volume ratio of 3:8. Typically an 11 mL volume of this mixture was horn ultrasonicated at 40% amplitude (Vibracell, Sonics & Materials Inc., CT) for 10 min to break apart loosely aggregated GO particles into single graphene oxide sheets. Under stirring, 1 mL of a prediluted mixture of 1-ethyl 2-methyl imidazolium tetrafluoroborate ($EMImBF_4$) in water was then added to the suspension. The electrodes were made by drop-casting the resulting suspension (450 μl) onto 1.5 cm diameter Pt discs (99.9%) and allowed to dry overnight. The dried films were then placed in an ashing furnace (Model 47900, Barnstead-Thermolyne, NH) under flowing $N_2$ and ramped to 300° C. at 20° C./min. The samples were not held at 300° C. but allowed to furnace cool immediately to prevent significant loss of $EMImBF_4$ due slow vaporization at elevated temperatures (Earle et al. *Nature* 2006, 439, 831). The mass of the films was determined by weighing the Pt before coating and after the application of the coating and thermal treatment.

An extra electrode was coated in each batch so that the resulting film could be scraped off and analyzed by thermal gravimetric analysis (TGA, 449 C Jupiter, Erich Netzsch GmbH & Co., Germany) to verify the fraction of $EMImBF_4$ in each electrode. The mass of graphene on each electrode was determined by multiplying the total mass of the reduced film by the mass fraction of graphene determined by TGA. Typically films contained approximately 1 mg of active material.

Characterization of Films

The graphene oxide was analyzed by atomic force microscopy before and after reduction using contact-mode AFM, carried out with a MultiMode/Digital Nanoscope IIIa system (Veeco Instruments) using NPS-type tips. Electrodes were also characterized by scanning electron microscopy (SEM, VEGA1, Tescan USA) at 20 kV acceleration voltage using both secondary and backscattered electron detectors.

The C/O ratios of graphene oxide and graphene before and after reduction were estimated using EDS (INCA x-act, Oxford Instruments, UK) by compressing the graphene oxide or graphene with a KBr pellet pressing die. The accuracy of such a measurement was verified using calibration standards created with similarly prepared samples of graphene oxide or graphene with C/O ratios that had been previously determined by combustion analysis (Atlantic Microlabs, GA). Fourier transform infrared spectroscopy (FTIR) was performed using a Nexus 670 FT-IR (Thermo Nicolet, Japan) instrument using FGSs finely dispersed in KBr. Powder X-ray diffraction (XRD) was carried out using a Miniflex II (Rigaku Americas, Cu Kα radiation).

Figure 2:
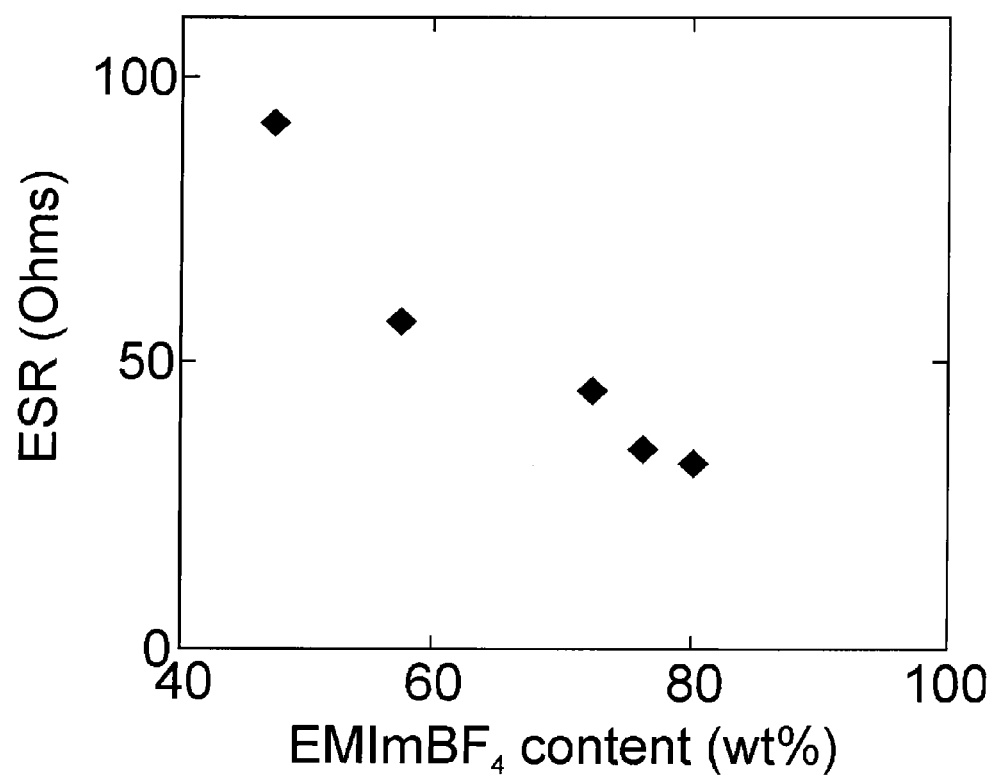
FIG. 2 is a plot showing equivalent surface resistance of coassembled and thermally reduced composites of graphene oxide with varying amounts of the ionic liquid 1-ethyl-2-methylimidazolium tetrafluoroborate.

Electrochemical testing of the electrodes was carried out in a two-electrode configuration using a spring-loaded stainless steel test cell (MTI Corp. CA) and a Celgard 3501 membrane separator that had been saturated with $EMImBF_4$. Electrodes were assembled in an Ar filled glovebox (Innovative Technology, MA). Each electrode was placed in the test cell and 10 μL of $EMImBF_4$ was added between each electrode and the presoaked membrane to ensure an excess of $EMImBF_4$ was supplied to every electrode. Cyclic voltammetry, electrochemical impedance spectroscopy (EIS) and galvanostatic charge/discharge tests and were carried out on assembled test cells using a computer-controlled potentiostat (VSP, Bio-Logic USA). The capacitance was estimated by cyclic voltammetry using a scan rate of 5 mV/s and a potential window of 3 V. The results are shown plotted in FIG. 1 as a function of 1-ethyl 2-methylimidazolium tetrafluorobrate ($EMImBF_4$) wt %. The equivalent series resistance of (ESR) of the devices was measured using galvanostatic discharge testing at current densities of between 1 and 10 A/g at a potential of 3 V. Capacitors with lower ESRs can be charged and discharged more rapidly, which effectively increases their power densities. FIG. 2 shows the results plotted as a function of 1-ethyl 2-methylimidazolium tetrafluorobrate ($EMImBF_4$) wt %.

The invention claimed is:

1. A method of making a graphene-ionic liquid composite, comprising combining a graphene source with at least one ionic liquid and heating the combination at a temperature of 200° C. to 450° C.: wherein the graphene source is fully exfoliated single planar sheets of graphite that are approximately ≤1 nm thick; and wherein the at least one ionic liquid comprises 1-ethyl-2-methylimidazolium tetrafluoroborate.

2. The method of claim 1, wherein the at least one ionic liquid further comprises a member selected from the group consisting of 1-alkyl-3-methylimidazoliumtetrafluoroborates, 1-butyl-3-methylimidazolium hexafluorophosphate ([BMIM][$PF_6$]), 1-butyl-3-methylimidazolium hydroxide [bmim]OH), 1-ethyl-3-methylimidazolium dicyanamide, 1-butyl-3-methylimidazolium chloride, 1-butyl-3-methylimidazolium hexafluorophosphate, trioctylmethylammonium bis(trifluoromethyl-sulfonyl)imide, 1-butyl-3-methylimidazolium chloride, 2-Hydroxyethylammonium formate, 1,3-dialkyl-1,2,3-triazolium hexafluorophosphates, 1,3-dialkyl-1,2,3-triazolium bistriflimides, 1,3-dialkylimidazolium hexafluorophosphates, 1,3-dialkyl-1,2,3-triazolium bistriflimides, triethylsulfonium bis(trifluoromethylsulfonyl)imide, bis(pentafluoroethylsulfonyl)imide, 1-butyl-1-methylpiperidinium tetrafluoroborate, choline acetate, 1-butyl-1-methylpiperidinium hexafluorophosphate, 4-ethyl-4-methylmorpholinium methyl carbonate 1-ethyl-1-methylpiperidinium methyl carbonate, triethylsulfonium bis(trifluoromethylsulfonyl)imide, and 2-hydroxyethylammonium formate.

3. The method of claim 1, wherein the graphene source is dispersed in at least one solvent, wherein the at least one solvent comprises an organic solvent.

4. The method of claim 1, wherein the combination is applied to a substrate prior to heating by a casting method or a printing method.

5. The method of claim 4, wherein the substrate is a metal.

6. The method of claim 4, wherein the substrate is current collector.

7. A method of making an electrode, comprising combining a graphene source with at least one ionic liquid, coating the combination onto a substrate and heating the combination at a temperature of 200° C. to 450° C., wherein the graphene source comprises fully exfoliated single planar sheets of graphite that are approximately ≤1 nm thick; and wherein the at least one ionic liquid comprises 1-ethyl-2-methylimidazolium tetrafluoroborate.

8. The method of claim 7, wherein the at least one ionic liquid further comprises a member selected from the group consisting of 1-alkyl-3-methylimidazoliumtetrafluoroborates, 1-butyl-3-methylimidazolium hexafluorophosphate ([BMIM][$PF_6$]), 1-butyl-3-methylimidazolium hydroxide ([bmim]OH), 1-ethyl-3-methylimidazolium dicyanamide, 1-butyl-3-methylimidazolium chloride, 1-butyl-3-methylimidazolium hexafluorophosphate, trioctylmethylammonium bis(trifluoromethyl-sulfonyl)imide, 1-butyl-3-methylimidazolium chloride, 2-Hydroxyethylammonium formate, 1,3-dialkyl-1,2,3-triazolium hexafluorophosphates, 1,3-dialkyl-1,2,3-triazolium bistriflimides, 1,3-dialkylimidazolium hexafluorophosphates, 1,3-dialkyl-1,2,3-triazolium bistriflimides, triethylsulfonium bis(trifluoromethylsulfonyl)imide, bis(pentafluoroethylsulfonyl)imide, 1-butyl-1-methylpiperidinium tetrafluoroborate, choline acetate, 1-butyl-1-methylpiperidinium hexafluorophosphate, 4-ethyl-4-methylmorpholinium methyl carbonate 1-ethyl-1-methylpiperidinium methyl carbonate, triethylsulfonium bis(trifluoromethylsulfonyl)imide, and 2-hydroxyethylammonium formate.

9. The method of claim 7, wherein the substrate is a metal.

10. The method of claim 7, wherein the substrate is current collector.

11. The method of claim 7, the step of coating the combination onto the substrate comprises a casting method and/or a printing method.

12. The method of claim 7, wherein the electrode has a specific capacitance of about 140 F/g, wherein the at least one ionic liquid is present in the composite at 75 wt % or more.

13. The method of claim 7, wherein the electrode has an equivalent series resistance of up to 48 Ohms, wherein the at least one ionic liquid is present in the composite at 75 wt % or more.

14. The method of claim 7, wherein the composite comprises no more that about 0.1 wt % solvent after heating.

15. The method of claim 1, wherein the combination comprises no more than about 0.1 wt % solvent after heating.

* * * * *